United States Patent [19]

Lucas

[11] Patent Number: 4,720,764
[45] Date of Patent: Jan. 19, 1988

[54] OPERATOR STATIC GROUNDING CORD
[75] Inventor: Derek A. Lucas, Norwell, Mass.
[73] Assignee: Alden Research Foundation, Brockton, Mass.
[21] Appl. No.: 20,479
[22] Filed: Mar. 2, 1987
[51] Int. Cl.⁴ .............................................. H05F 3/02
[52] U.S. Cl. ..................................... 361/212; 361/220
[58] Field of Search ................. 361/212, 220; 340/649
[56]  References Cited
U.S. PATENT DOCUMENTS
4,605,984  8/1986  Fiedler ................................ 361/220

*Primary Examiner*—L. T. Hix
*Assistant Examiner*—David M. Gray
*Attorney, Agent, or Firm*—James H. Grover

[57]  ABSTRACT

Apparatus for draining the static charge from an operator handling discharge-sensitive electronic components has an electrode module applied to the operator's wrist connected to a grounding module by a two conductor loop which includes a lamp, a battery and a switch which, when closed, lights the lamp if one of the conductors is continuous between the electrode and grounding terminal.

17 Claims, 3 Drawing Figures

OPERATOR STATIC GROUNDING CORD

BACKGROUND OF THE INVENTION

In the assembly of electronic circuits it is possible that a previously tested electronic component, such as an integrated circuit chip, is damaged by static discharge from the hands of the person assembling the circuit. The damage is more serious than the loss of the single component since the cost of locating the defect in the circuit requires time and skill and can be higher than the value of the component. Therefore it has become the practice in manual circuit assembly of static sensitive components to connect the assembly operator to ground and continuously bleed off any static charge which may develop in the operator. Grounding is accomplished by a conductor having at one end a connector attached to a grounded terminal at the assembly station, and at its other end an electrode pressed against the operators skin as by a conductive wrist strap, for example.

However, the prior grounding assembly of wrist electrode, conductor and ground connector is repeatedly flexed by the assembly operator's arm movements and is subject to fatigue failure or by abusive treatment which breaks the connection between the conductor and the ground connector or the wrist electrode. Usually such failures cannot be visually detected and negate the grounding precautions taken to protect static sensitive components. An obvious solution is to apply an electrical continuity tester to the ground connector and wrist electrode. But this usually requires removal of the wrist strap or is impractical. Another test for integrity of the grounding system is with a specialized instrument which accepts contact by both the operator's fingers and the ground connector. Such instruments are expensive and inconveniently occupy area at the assembly station.

Accordingly it is the object of the present invention to provide a way of testing the integrity of static grounding apparatus which can be used with or without detaching the apparatus, and which does not require expensive or space consuming test instruments at the operator's station.

SUMMARY OF THE INVENTION

According to the invention electrical apparatus for draining a static charge from an operator to an electrical ground comprises an electrode for electrical connection to the operators body; a terminal for connection to ground; and a circuit connected between the electrode and ground terminal, wherein the circuit includes: a battery, switching means, a current indicator, and first and second conductors connected between the electrode and ground terminal and forming a loop including the battery, switching means and indicator in series such that closing of the switching means completes a current path through both conductors and the indicator signals integrity of the connection from the body electrode to the ground terminal.

DRAWINGS

DESCRIPTION

Figure 1:
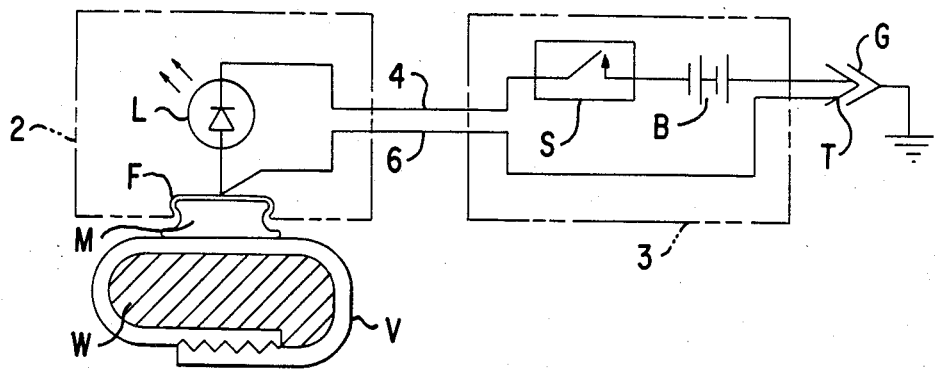
FIG. 1 is a schematic circuit drawing of operator grounding apparatus including an electrode module and a grounding module.

FIG. 1 illustrates schematically apparatus for draining the static charge from an operator assembling electronic components sensitive to static discharge such as integrated circuit chips. The operators body is represented by his wrist W about which is clasped an electrically conductive strap V, for example, of material sold under the trademark Velcro. The conductive wrist strap comprises an electrode electrically and mechanically connected with male M and female F metallic snap fasteners to a wrist module 2, shown in FIG. 2. The wrist module 2 is connected by two conductors 4 and 6 to a grounding module 3, shown in FIG. 3. A connection is made in the grounding module 3 to a ground terminal T such as a banana plug, spade lug or a like connector adapted to plug or screw into a mating receptacle G which is connected to ground.

Figure 2:
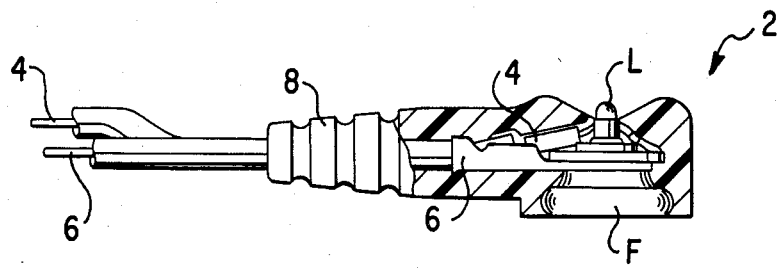
FIG. 2 is a side elevation, partly in section, of the electrode module attached to the wrist of an operator.
Figure 3:
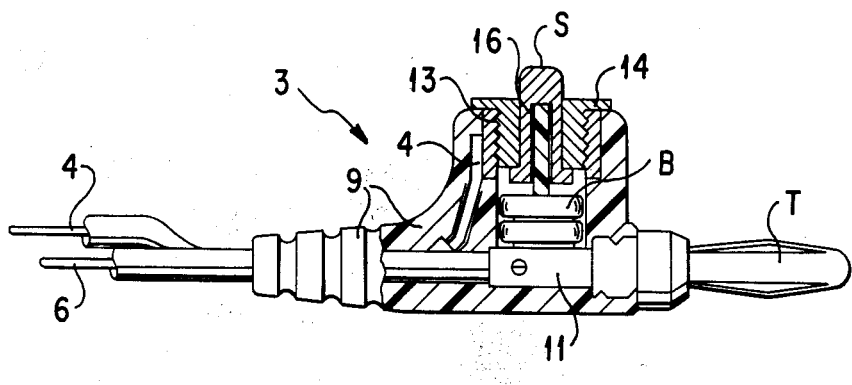
FIG. 3 is a side elevation, partly in section, of the grounding modules.

The wrist module 2 of FIGS. 1 and 2 comprises a jacket 8 of insulative thermoplastic molded around the upper part of the female snap fastener F, the insulation of the two conductors 4 and 6 and the base of the light emitting diode L. In the wrist module one of the conductors 6 is connected directly to the female snap fastener and to one electrode of the light emitting diode L. The other conductor 4 is connected between the other electrode of the diode and the grounding module 3.

The grounding module 3 has a thermoplastic insulative jacket 9 around the insulation of conductors 4 and 6, and around the shank 11 of the banana plug ground terminal T. One of the conductors 6 is connected directly to the banana plug shank. The other conductor 4 is soldered to an outer sleeve 13 with an internal thread removably receiving a threaded inner sleeve 14. Slide-fitting within the inner sleeve 14 is a plunger which comprises a normally open manual switch S. The outer and inner sleeves and the plunger are of tin plated brass. The switch plunger 5 has an axial bore receiving a cylinder of insulative elastomer such as silicone rubber which yielding urges the plunger away from contact with two cells B of a battery current source. The lower of the two cells makes direct contact with the shank 11 of the banana plug 12. When the plunger is depressed, the normally open switch 3 completes a circuit passing through a loop including the two conductors 4 and 6, the shank 11 of the banana plug, the battery B and the light emitting diode L which then lights as an indicator of continuity and integrity of the connection between the female snap fastener of the electrode and the banana plug of the grounding terminal T. This integrity and continuity test can be made with or without detaching the grounding terminal T from its ground receptacle and does not involve added test equipment in the operator's working area but is self contained with little more bulk than prior static grounding cords. The battery, switch and lamp may be rearranged in one module, or in different locations than shown, but there is an advantage in distributing the bulk and weight of the smaller light emitter in the wrist electrode module and the switch and batteries in the grounding module.

It should be understood that the foregoing description is for the purpose of illustration only and this invention includes all modifications and equivalents which fall within the scope of the appended claims.

I claim:

1. Electrical apparatus for draining a static charge from an operator to an electical ground comprising:

an electrode for electrical connection to the operator's body;
a terminal for connection to ground; and
a circuit connected between the electrode and ground terminal, wherein the circuit includes:
a battery,
switching means
a current indicator, and
first and second conductors connected between the electrode and ground terminal and forming a loop including the battery, switching means and indicator in series such that closing of the switching means completes a current path through both conductors and the indicator signals integrity of the connection from the body electrode to the ground terminal.

2. Apparatus according to claim 1 wherein the loop passes through the ground terminal.

3. Apparatus according to claim 1 wherein the switching means is a manual switch.

4. Apparatus according to claim 1 wherein the switching means is normally open.

5. Apparatus according to claim 1 wherein the switch is at the ground terminal end of the conductors.

6. Apparatus according to claim 1 wherein the current indicator is a light emitter.

7. Apparatus according to claim 1 wherein the indicator is at the electrode end of the conductors.

8. Apparatus according to claim 1 including a first insulative jacket around a part of the body electrode.

9. Apparatus according to claim 8 wherein the indicator is in the first jacket.

10. Apparatus according to claim 9 including a second jacket around a part of the ground terminal.

11. Apparatus according to claim 10 wherein the switching means is in the second jacket.

12. Apparatus according to claim 10 wherein the battery is in the second jacket.

13. Apparatus according to claim 1 including an insulative jacket around a part of the ground terminal.

14. Apparatus according to claim 13 wherein switching means is in the jacket.

15. Apparatus according to claim 13 wherein the battery is in the jacket.

16. Apparatus according to claim 1 wherein one conductor is continuous from the body electrode to the ground terminal.

17. Apparatus according to claim 16 wherein the other conductor is isolated from the ground terminal by the switching means.

* * * * *